United States Patent [19]

Ito et al.

[11] Patent Number: 5,583,054
[45] Date of Patent: Dec. 10, 1996

[54] DETERMINATION AND DETECTION OF ANTIBODY AND ITS IMMUNOGLOBULIN CLASS

[75] Inventors: Michio Ito; Minoru Ogura, both of Yokohama; Hideki Kohno, Kawasaki, all of Japan

[73] Assignee: Mitsubishi Kasei Corporation, Tokyo, Japan

[21] Appl. No.: 312,431

[22] Filed: Sep. 26, 1994

Related U.S. Application Data

[63] Continuation of Ser. No. 64,370, May 19, 1993, abandoned, which is a continuation of Ser. No. 557,390, Jul. 24, 1990, abandoned.

[30] Foreign Application Priority Data

Jul. 28, 1989 [JP] Japan ................................. 1-195968
Jun. 20, 1990 [JP] Japan ................................. 2-162056

[51] Int. Cl.$^6$ ............................................. G01N 33/543
[52] U.S. Cl. ........................ 436/523; 436/513; 436/526; 436/528; 436/529; 436/531; 436/524; 436/525
[58] Field of Search ....................... 436/513, 523, 436/524, 525, 526, 528, 529, 531, 534

[56] References Cited

U.S. PATENT DOCUMENTS

| | | | |
|---|---|---|---|
| 4,115,535 | 9/1978 | Glaver | 436/526 |
| 4,279,617 | 7/1981 | Masson et al. | 436/509 |
| 4,434,227 | 2/1984 | Unger | 435/5 |
| 4,829,012 | 5/1989 | Cambiaso et al. | 436/512 |
| 4,952,622 | 8/1990 | Chauvel et al. | 524/376 |
| 5,132,210 | 7/1992 | Adams et al. | 436/518 X |

FOREIGN PATENT DOCUMENTS

| | | | |
|---|---|---|---|
| 2531223 | 8/1983 | European Pat. Off. | |
| 0194156 | 9/1986 | European Pat. Off. | |
| 0291389 | 5/1988 | European Pat. Off. | |
| 0177265A | 9/1985 | Japan | 436/523 |
| 2125547 | 3/1984 | United Kingdom | |
| WO89/01161 | 7/1988 | WIPO | |
| 8904373 | 5/1989 | WIPO | 436/526 |

OTHER PUBLICATIONS

An 85-265974 & JP-A≠60 177 265 (Japanese Synthetic Rubber) 11 Sep. 1985; World Patents Index Latest, Week 8543, Derwent Publications Ltd., London, GB.

*Primary Examiner*—Lila Feisee
*Assistant Examiner*—Susan C. Wolski
*Attorney, Agent, or Firm*—David G. Conlin; David S. Resnick; Dike, Bronstein, Roberts & Cushman, LLP

[57] ABSTRACT

The present invention provides a method for determining the presence of a class of an antibody in a biological sample. In this method, a first reagent including insoluble particles having an antigen to the antibody immobilized on the surface thereof, and a second reagent including insoluble magnetic particles having immobilized on the surface thereof a substance particularly reactive to a specific immunoglobulin class, is reacted with the sample under conditions to promote agglutination of the first and second reagents with the antibody. The unreacted second reagent and the agglutinate are separated from the unreacted first reagent by application of a magnetic field. Then the amount of unreacted first reagent is determined.

19 Claims, 3 Drawing Sheets

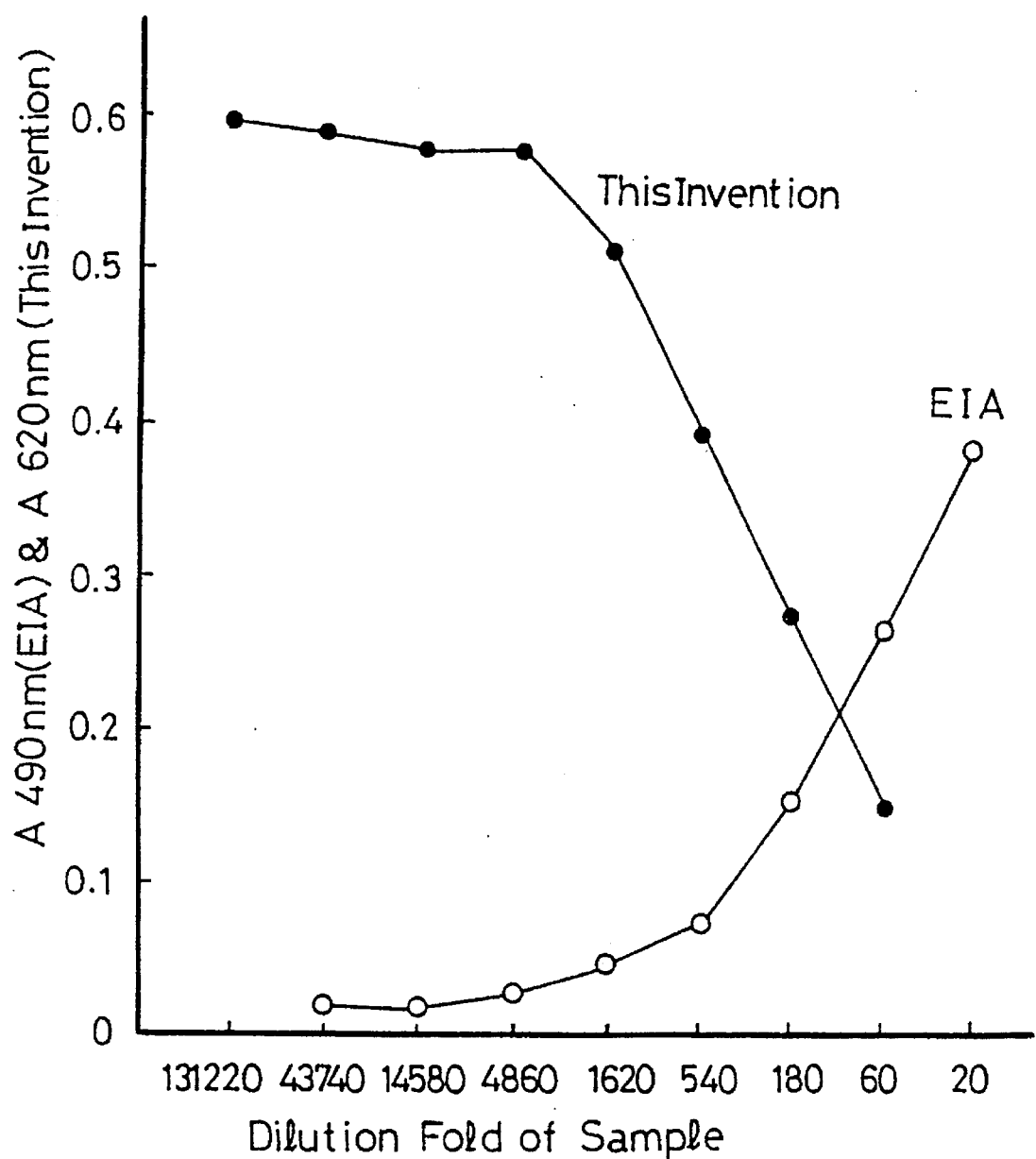
F I G. 1

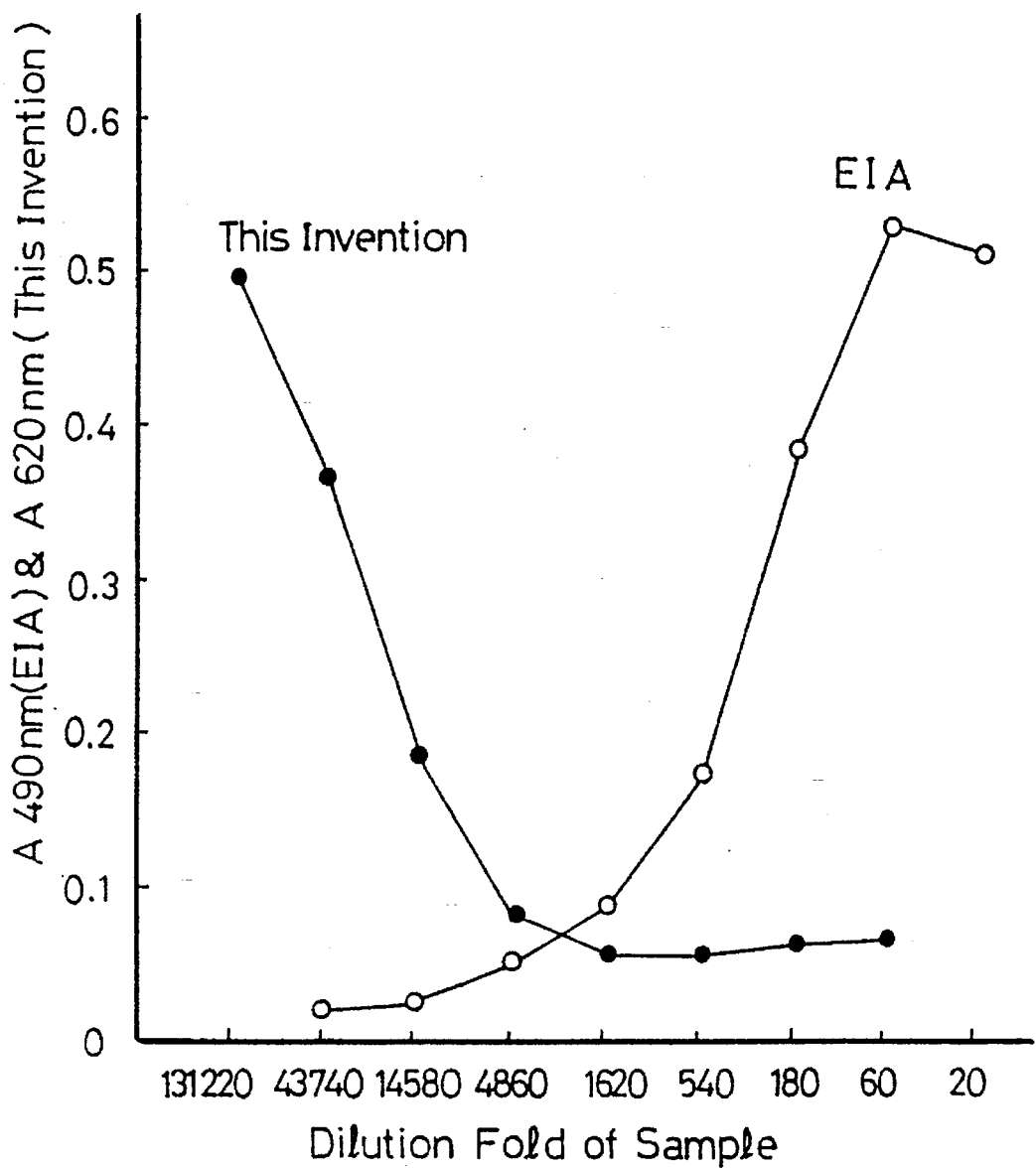
F I G. 2

1

DETERMINATION AND DETECTION OF ANTIBODY AND ITS IMMUNOGLOBULIN CLASS

This is a continuation of application Ser. No. 08/064,370 filed on May 19, 1993, now abandoned, which is in turn, a continuation of Ser. No. 07/557,390, filed Jul. 24, 1990, now abandoned.

FIELD OF THE INVENTION

This invention relates to a method for determining in a biological fluid sample an antibody against a specific antigen and identifying the immunoglobulin class of the antibody. Particularly, it relates to a method for determinating and detecting an antibody, which may advantageously be used as a clinical test such as serum test for the diagnosis or diffferential diagnosis of infectious disease or autoimmune disease in the field of clinical medicine.

BACKGROUND OF THE INVENTION

In an infectious disease or autoimmune disease, an antibody against a specific antigen which is inherent in the disease appears in serum of a patient. In the conventional clinical test, it has simply been examined whether or not the serum contains the antibody. But in recent years, determination of the amount of the antibody and classification of its immunoglobulin class (IgG, IgA, IgM, IgD and IgE in case of human beings has attracted attention in order to investigate the cause of the disease or morbid state precisely.

For example, in case of an conventional diagnosis of the infectious disease, the presence of the antibody against a pathogen of the infectious disease shows only the past history of the same infectious disease. However, if the change in an amount of the antibody and the class of immunoglobulin are ascertained, information concerning the time of infection or an advanced stage of the disease can be obtained. More specifically, as introduced in the journal of "Japan Clinics", Vol. 43, Autumn Special Issue, Second volume, page 27 (1985) with the title of "Interpretation of assay results of virus antibody", the detection of IgM antibody is required for the diagnosis of rubella.

Even if immunoglobulins to be assayed are in the same antibody class, it may be desirable to determine which kind of an antigen they react with among many kinds of antigens. For example, in the diagnosis of allergies the most important immunoglobulin class is IgE, and the RAST method (radioallergen adsorbent test) has been practiced as an available test method, wherein the kind of allergen as an etiogenic substance is identified and the amount of IgE reacting with the allergen is measured.

In this field RIA and EIA are both methods which have taken the leadership as a quantitative assay method. RIA and EIA are not only capable of carrying out a quantitative determination of high sensitivity, but also capable of identifying the immunoglobulin class to be assayed, so that they are significant in the diagnosis. However, these methods have disadvantages that they require to separate and wash the antibody reacted with the antigen so that the operation is complicated and takes much time. Also, in operations in which the sample should be treated many times, such as when separating and washing steps, are required, a danger of infection from the sample cannot be ignored. In addition, RIA involves many difficulties in handling, such as the problem in radioactive waste and the necessity for specific equipment. EIA has problems in that reaction time and temperature must be controlled strictly and that it is likely affected by an interfering reaction, since an enzyme is used as a labelling substance.

As to other assay techniques for the antibody in the field of the diagnostic, there can be mentioned passive blood cell agglomeration and a latex agglomeration, in addition to the above RIA and EIA. However, these methods have disadvantages in that they are limited only to a qualitative diagnosis, that the immunoglobulin class cannot be identified, and that the detection sensitivity is relatively low. For overcoming such problems partially, there is disclosed a method for detecting the immunoglobulin class of the antibody using an antigen-carrying magnetic particles and blood cells carying anti-globulin antibody (Japanese Patent Application Laid-Open (KOKAI) No. 177265/1985).

For identifying the class of the antibody to a specific antigen and determining the amount thereof present by using the above agglomeration method, it is necessary to measure the amount of agglomeration produced by the reaction between the antigen-carrying particles and the antigen-reactive antibody in the sample. In this event, the agglomeration of antibodies may sometimes occur due only to the antigen-carrying particle. In addition agglomeration of the particles carrying the anti-antibody which is specific to the immunoglobulin class of said antibody, may possibly occur as well due to immunoglobulins which are non-bindable to said antigen and are present in the sample serum in a large amount. Therefore, there still remain several problems without resolution. For example, undesirable steps which contain the most troublesome operations such as washing and resuspending are still required in the the subsequent steps. For example, the antigen-carrying particles is first reacted with a sample, and the reaction mixture is then separated and washed to remove the immunoglobulins which are non-bindable to said antigen, and then insoluble particles carrying the substance specific to the immunoglobulin class of the antibody are reacted therewith. Also, the time period for completing the assay is relatively long. Detection sensitivity is in addition inferior to that of RIA or EIA.

In the publication of WO 89/01161, there is disclosed a method in which magnetic material-containing particles carrying a monoclonal antibody thereon and an antigen in a specimen are reacted, followed by reaction with insoluble particles carrying an antibody thereon but containing no magnetic particles, then applying a magnetic field thereto to separate unreacted magnetic material-containing particles from agglomerated bulk comprising said two kinds of particles and the antigen, and measuring an amount of the remaining antibody-carrying insoluble particles. In this method the amount of the antigen in the specimen can be determined from the degree of decrease in turbidity. However, there is no description concerning the identification of the immunoglobulin class of the antibody. Thus, it has been desired to develop an assay method with high sensitivity, which can determine an amount of the antibody, can identify the immunoglobulin class of the same and can complete the assay within a short time.

SUMMARY OF THE INVENTION

The inventors of the present invention have found that the reaction between antigen-carrying substrate particles and antigen-reactive antibody in a sample can be quantitatively determined and detected, not directly by estimating the amount of agglomeration produced by the reaction in the sample, but indirectly by estimating the remaining unreacted components in the reaction mixture from which the agglomeration is removed, and that the agglomeration can be easily separated from the unreacted components by using a magnetic material-containing substrate carrying a substance which is particuraly reative to a specific immunoglobulin class. As the results of further intensive studies, they have additionally found that separating and washing may suprisingly be omitted after the reaction between the antigen and the antibody in the sample, which are essential in the conventional methods, and that a high sensitivity superior to that of EIA may be obtained within a shorter period of time than in the conventional methods.

An object of the present invention is to provide a safe method of determination and detection of an antibody, which has a high sensitivity superior to that of RIA or EIA and makes it possible to determine the amount of the antibody and to identify its immunoglobulin class without carrying out complicated separating and washing operations.

In accordance with the present invention, therein provided a method for the determination and detection in a biological fluid sample of an antibody against a specific antigen and of its immunoglobrin class, comprising the steps of:

(a) reacting simultaneously with the sample a first reagent comprising insoluble particles having immobilized on the surface thereof an antigen capable of specifically binding to the antibody and a second reagent comprising insoluble magnetic material-containing particles having immobilized on the surface thereof a substance particularly reactive to a specific immunoglobulin class, under conditions to promote agglutination of the first and second reagents with the antibody to form an agglutinate;

(b) separating locally in a reaction system unreacted second reagent and the agglutinate from unreacted first reagent by applying a magnetic field;

(c) determining the amount of unreacted first reagent; and (d) correlating the amount determined in step (c) with the amount of the antibody present in the sample.

BRIEF DESCRIPTION OF THE DRAWINGS

FIG. 1 is a drawing which shows the reactivity of IgG class rheumatoid factor with a dilution series of a serum sample of a rheumatoid patient determined according to the present invention (solid circle) and EIA method (white circle), in which the reactivity is shown by absorbance. FIGS. 2 and 3 are drawings showing the reactivity of IgA and IgM class rheumatoid factors with the same samples as in FIG. 1, respectively.

DESCRIPTION OF THE PREFERRED EMBODIMENTS

Figure 3:
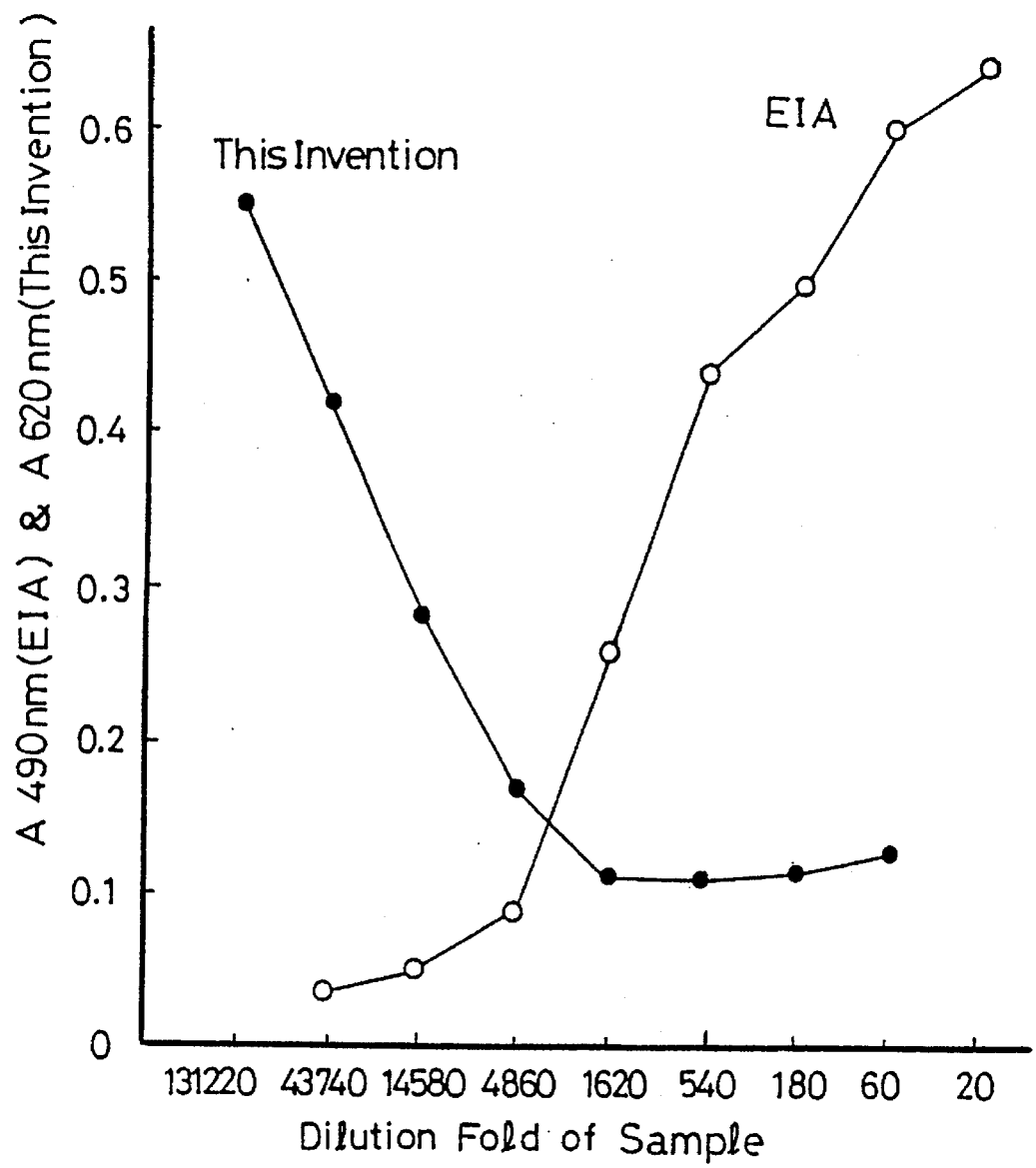

The "antigen" referred to in the present invention includes both a single antigen or a mixture of antigens, which is selected for a specific object such as diagnosis, among all the substances having an ability of causing production of an antibody in human being or an animal. For example, in the case of diagnosis of infectious disease, there can be mentioned virus, bacteria, or specific proteins and saccharide chains which constitute those virus and bacteria.

As the "insoluble substrate particles" of the first reagent for carrying the antigen, there may be used, for example, cells such as erythrocytes, gelatin particles, microcapsules such as liposomes, organic polymer substances such as latex particles of polyvinyltoluene and polystyrene, inorganic fine particles such as carbon black, or colloidal particles of various metals or metal compounds, but those having excellent dispersibility in a reaction medium and small sedimentation by themselves are preferred for the spectrophotometric determination.

A "substance particularly reactive to a specific immunoglobulin class" means a substance having an ability of binding to an antibody by selectively recognizing characteristics of the antibody molecule, for instance, an antibody against IgG, IgA, IgM, IgD, IgE or L(light)-chains thereof; protein A; and $Cl_q$ which are types of complement components. However, the "substance" does not include those which are bindable to the antibody through an antibody activity possessed by said immunoglobulin itself, i.e., a substance which reacts as an antigen with said immunoglobulin.

As the "insoluble substrate particles" of the second reagent containing the magnetic material, there may be used polysaccharides such as agarose, dextran and carboxymethyl cellulose, proteins such as gelatin and polymerized albumin and protein derivatives, and more preferably synthetic polymers obtained by polymerization of aromatic vinyl compounds such as styrene and divinylbenzene and/or methacrylate derivatives.

As the "magnetic material" which said second reagent particles should contain, preferred are iron, magnetic iron oxide such as tri-iron tetroxide, and their mixtures or alloys with other metal or metal oxide. The magnetic material advantageously has no residual magnetization. Also the average particle size of the magnetic material is preferably 10 to 200 Å in diameter. The amount of these materials which the second reagent particles contains is, preferably at least 5% by weight of the second particles, more preferably, 15 to 65% by weight.

The average particle size of the first reagent particles and of the second reagent particles are 0.1 to 10 μm in diameter, preferably 0.2 to 3 μm in diameter. As a combination of both particles, there may be used a combination of the first reagent particles having an average particle size of 0.5 to 3 μm and the second reagent particles having an average particle size of 0.2 to 2 μm, preferably, a combination of the first reagent particles having an average particle size of 1 to 2.5 μm and the second reagent particles having an average particle size of 0.5 to 1.5 μm. With respect to the average particle sizes of such particles, if the average particle size of the first reagent particles is too small, the surface area per unit weight becomes so large that the amount of the carried antigen becomes also large, whereby agglomeration between the first reagent particles will likely be caused. When the determination of this invention is carried out using a light of a wavelength of 600 to 1000 nm, which is a range less affected by the sample component, this agglomeration reaction is undesirable since it increases turbidity and causes lowering in sensitivity. Such agglomeration reactions may also occur when the average particle size of the second reagent particles is too large. Furthermore, in the case where the average particle size of the first reagent particles is too large, natural sedimentation of the particles is promoted, and in case that the average particle size of the second reagent particles is too small, and separation by a magnetic field takes much time. Accordingly, these cases are not practical.

For carrying the antigen or the substance particularly reactive to the specific immunoglobulin class on the substrate particles, either of physical adsorption or chemical adsorption based on covalent bonding of functional groups may be used.

The ratio of the amounts of the first or second insoluble substrate particles and the antigen or substance to be carried thereon is not particularly limited, but when 5 to 200-fold amounts of the substrate particles in weight ratio to the antigen or substance are used, good results can in general be obtained.

In accordance with the present invention a sample solution which possibly contains an antibody is mixed and reacted with insoluble substrate particles carrying the antigen thereon and the magnetic material-containing particles carrying the substance particularly reactive to the specific immunoglobulin class in a reaction system. Stirring at an initial stage of the reaction should be carried out to mix homogenously, and thereafter the reaction may proceed without stirring. The pH in the reaction is preferably 5 to 10, more preferably 7 to 9 as in the typical immunochemical reaction. The temperature of the reaction is in the range of 2° to 50° C., desirably of a room temperature to 37°–40° C. The reaction time may be optional from a very short period of time to one day and night, but in view of sensitivity and operability, it is usually set within the range of 5 to 60 minutes. These reaction conditions are the same in the subsequent procedural steps.

The desired pH range is usually maintained by a buffer. As the buffer, for example, a phosphate and tris(hydroxymethyl)aminomethane can typically be used, but in general almost all the buffers from neutral to weak alkaline can be used. In general, salts such as sodium chloride and proteins such as bovine serum albumin are added in order to avoid nonspecific reactions.

When a sample is mixed with the antigen-carrying insoluble substrate particles and the magnetic material-containing particles carrying the substance which is particularly reactive to the certain immunoglubulin class, the antibody in the sample reacts with the antigen at the surface of the substrate particles and further the antibody bound to the antigen binds to the substance carried on the magnetic material-containing particles to cause agglomeration between the insoluble substrate particles and the magnetic material-containing particles. In this case, either of binding between the antigen carried on the insoluble substrate particles and the antibody in the sample or binding between the antibody in the sample and the substance carried on the magnetic material-containing particles may take place sequentially or simultaneously. However, it is more preferred to react the antibody in the sample firstly with the antigen-carrying insoluble substrate and then with the magnetic material-containing particles carrying the substance particularly reactive to the certain immunoglobulin class. This is because improvement in sensitivity can be more expected than the reverse case due to advancement in reaction-efficiency of the magnetic material-containing particles.

The ratio of the above antigen-carrying insoluble substrate particles and the magnetic material-containing particles carrying the substance particularly reactive to the specific immunoglobulin class to be used may be selected from the range of 1:20 to 20:1, preferably 1:4 to 4:1. If either of the particles deviates from this range, the sensitivity will be lowered since the agglomeration of the antigen-carrying insoluble substrate particles with each other or that of the magnetic material-containing particles with each other will possibly occur.

As to the reaction between the antigen-carrying insoluble substrate and the antibody in the sample, the following two instances can be considered:

1) one molecule of the antibody binds to two particles, so as to cause agglomeration.
2) one molecule of the antibody reacts with only one particle, so that no agglomeration between particles occurs.

In a conventional assay method on the basis of the latex agglomeration reaction, it is preferred that the reaction of the instance 2) occurs in a smaller quantity, since the result of the above 1) is detected. In the present invention, however, less of the instance 1) and more of the instance 2) are desired. This is because the reaction 1) can occur regardless of the class of the antibody and it affects the spectrophotometric determination, whereby the precision in determination of each antibody class is lowered.

As to the specific manner to cause both less of the reaction 1) and more of the reaction 2), there may be mentioned as follows:

(1) to carry the antibody on the first reagent particles with high density by the physical adsorption or covalent bonding, (2) to use first reagent particles having the average size of about 1 μm or more, preferably 1 to 2.5 μm, which is larger than that of the insoluble substrate particles having the average size of about 0.1 to 0.8 μm conventionally employed, thereby increasing the density of the antigens per unit surface of the first reagent particle.

(3) to lower the concentration of the first reagent particles in the reaction mixture or use the first reagent particles having the average particle size of about 1 μm or more, preferably 1 to 2.5 μm and high a specific gravity which does not cause the natural sedimentation, thereby decreasing the collision of the particles, i.e., collision probability between them.

However, the aforesaid factors to cause lowering in precision are acceptable so long as they do not cause practical problems. In fact, the reaction 1) can be relatively restrained, or even if the reaction 1) occurs, the effects to the spectrophotometric determination results can be minimized by optionally selecting the amount of the antigen-carrying insoluble particles, the amount of the carried antigen, and the size of the particle. For instance, the average particle size of the antigen-carrying insoluble substrate particles is selected to be 1 to 2.5 μm, the average particle size of the magnetic material-containing particles is selected to be 0.5 to 1.5 μm and the ratio of the insoluble antigen-carrying substrate particles and the magnetic material-containing particles to be used is further selected to be 1:0.8 to 2.

Accordingly, the present invention is not limited only to the instance 2) in the reaction but includes both of the instances 1) and 2).

In the step of applying a magnetic field to the reaction system, it is preferred to utilize a magnetic strength and a reaction system which enable both of the magnetic material-containing particles and the agglomeration containing the magnetic material-containing particles to be easily separated in 5 to 20 minutes. If the time required for the separation is too short, this usually leads to low sensitivity and reproducibility, while a too long time leads to undesirable effects. For this reason, the reaction system with a relatively small size can be handled easily. For example, a microplate is employed for the system. The size of each well in the microplate such as a 96-hole microplate is small. Thus, when small magnets are placed at the spaces between each of the wells in the 96-hole microplate, determination can be easily carried out by using a microplate reader as in EIA utilizing the microplates. Therefore, the microplate is suitable for use in the present invention. As to the magnet for applying the magnetic field, a permanent magnet or an electromagnet can be used.

When the magnetic material-containing particles are separated by means of the magnetic field, the antigen-carrying substrate particles agglomerated with the magnetic material-containing particles are also separated. Consequently, the degree of the reaction of the antigen and antibody in the sample can be easily estimated by detecting the turbidity or the amount of the unreacted substrate particles suspended in the reaction solution after the separation. That is, the stronger the reaction between said antigen and antibody in the sample is, the less the turbidity (absorbance) becomes.

At this stage, it may occur that a part of the magnetic material-containing particles has not been separated, and is detected together with the unreacted antigen-carrying substrate particles. However, it is acceptable so long as the remaining magnetic material-containing particles do not cause practical problems.

The means to detect the turbidity includes, most simply, a visual observation with eyes under illumination on a black background, thereby roughly estimating the residual amount of the antigen-carrying insoluble substrate particles in the reactin solution depending on the degree of the turbidity. Use of various colorimeters or turbidimeters makes a presice quantitative determination possible. As to the wavelength for determination, a wavelength corresponding to a visible light or near infrared ray, preferably 600 to 1100 nm can be used. Moreover, by a flow cytometry method using a laser beam, the number of the residual particles may be directly counted.

For the quantitative determination, a calibration curve of the antibody should be previously obtained by using a sample having an pre-determined antibody concentration or a sample having a standard amount of an antibody, and plotting the resulting values to the concentration of the antibody in the sample. Thus, from the measured value the concentration of an sample unknown in concentration, the concentration of said antibody can be obtained.

EXAMPLES

The present invention will be hereinafter explained in more detail by referring to Examples, but it should be noted that the scope of the present invention is by no means limited thereto.

Example 1

Determination of anti-cardiolipin antibody

Preparation of reagents:
1) Preparation of a suspension of carbon powder carrying cardiolipin as an antigen thereon;

In 4 ml of ethanol was suspended and dispersed 10 mg of carbon powder (Thermal Carbon MT, produced by MITSUBISHI KASEI CORPORATION, particle diameter: 0.3 µm). The carbon powder was frequently subjected to an ultrasonic wave treatment to disperse it (same in the subsquent procedures, if necessary), since it is likely to sedimente and agglomerate. The carbon powder was then sedimented by centrifugation and the supernatant was removed. Then, 4 ml of ethanol solution containing 0.03% of cardiolipin, 0.03% of lecithin and 0.9% of cholesterol was added to the sediment followed by dispersion, and the dispersion was further stirred for 30 minutes to homogenize it.

Subsequently, to 3.2 ml of 0.1M phosphate bufferred saline solution, hereinafter referred to as "PBS", pH 7.4, vigorously stirred, was promptly added dropwise the whole amount of the carbon powder dispersion, and 16.4 ml of the PBS solution was added thereto followed by continuting the vigorous stirring for further 10 minutes to adsorb fat soluble components including the antigen on the surface of the carbon powder. After completion of the adsorption, the dispersion was centrifuged and the supernatant was removed. Then, 20 ml of phosphate buffer, pH 7.4, containing 10% of choline chloride was added to the sediment and then re-dispersed to obtain a desired reagent. The carbon powder suspension thus obtained has the same sensitivity as or more sensitivity than a commercially available product as a reagent for RPR method (a method of detecting anti-cardiolipin antibody by a visual inspection of carbon powder agglomeration), which is one of the assays for syphilis.

2) Preparation of a magnetic material-containing latex particles carrying anti-IgG, IgM antibody F(ab')$_2$ thereon;

An antiserum obtained by immunizing rabbit against human IgG or human IgM was adsorbed onto Bence Jones protein ($\chi$ and $\lambda$) to separate a specific antiserum to H-chain of IgG and IgM. Each fraction of anti-IgG and anti-IgM antibodies was collected from the resultant antiserum by a conventional method, and then digested with pepsin and subject to a molecular sieve column chromatography to obtain F(ab')$_2$.

On the other hand, 1 ml of a magnetic material-containing latex (Estapor SML266, particle size: 0.7 µm, 10%) produced by Rhone Poulenc Chimie was sufficiently mixed with 19 ml of distilled water followed by centrifugation (10000 rpm, 10 minutes), and then the supernatant was removed to obtain a washed latex pellet. To the pellet was added and dispersed an antibody solution dissolved 4 mg of anti-IgG or anti-IgM antibody F (ab')$_2$ previously prepared in 10 ml of 0.1M tris-hydrochloric acid buffer, pH 8, hereinafter referred to as "tris buffer". The dispersion was further stirred for one hour to carry F (ab')$_2$ on the surface of the magnetic material-containing latex. The dispersion was centrifuged again to remove the supernatant followed by re-dispersing, suspending and stabilizing with 10 ml of the tris buffer containing 0.3% of bovine serum albumin. The resultant latex was further centrifuged and suspended in 10 ml of tris buffer containing 0.05% of sodium azide, and preserved at 4° to 10° C.

Procedure of the determination:

Each of syphilis patient serum, which is positive (detection limit dilution: 16-fold) by the RPR method, and normal serum, which is negative by the same methol, was diluted with 0.1M tris hydrochloric acid buffer, pH 8.2, containing 0.1% of bovine serum albumin and 0.9% of salt, hereinafter referred to as "TBS buffer", to from 20-fold to 320-fold stepwisely by 2-fold, so as to prepare a diluted series of sera. Each of the samples of the diluted series and TBS buffer as a control was apportioned to two wells in 96-hole microplate with an amount of 100 µl. After each 50 µl of the cardiolipin antigen-carrying carbon powder suspension diluted to 2-fold with the tris buffer solution was apportioned thereto, and immediately a side of the microplate was tapped for 10 seconds to mix the contents in the wells and it was allowed to stand at a room temperature for 30 minutes to complete the reaction. On the other hand, each of the anti-IgG-carrying magnetic material-containing latex and anti-IgM-carrying magnetic material-containing latex was diluted to 8-fold with the tris buffer solution. They were respectivly apportioned with an amount of 50 µl to either one of the wells of each dillution. The microplate was then tapped as in the above to mix the contents and allowed to stand at room temperature for 10 minutes to complete the reaction. Then, by means of small sized rod magnets of 3 mm φ a magnetic field was applied to four sides walls of the each well of the microplate for 10 minutes to gather the magnetic material-containing latex to the side portions of the walls. Turbidity of the antigen-carrying carbon powder suspension which remained in the each well without reacting with the magnetic material-containing latex was determined with Microplate Reader (produced by Nippon Intermed Co., NJ-2000), using a light of a wavelength of 620 nm.

The results are shown in Table 1.

TABLE 1

| Dilution fold of sample | Negative sera | | Positive sera | |
|---|---|---|---|---|
| | Anti-IgG antibody | Anti-IgM antibody | Anti-IgG antibody | Anti-IgM antibody |
| Control | (0.371) | (0.379) | — | — |
| 20 | 0.358 | 0.345 | 0.141 | 0.031 |
| 40 | 0.367 | 0.342 | 0.198 | 0.103 |
| 80 | 0.363 | 0.351 | 0.241 | 0.193 |
| 160 | 0.367 | 0.354 | 0.279 | 0.250 |
| 320 | 0.361 | 0.351 | 0.312 | 0.270 |

Both of the anti-IgG or IgM antibody-carried magnetic material-containing latex were reacted with the diluted positive sera sample even when it is diluted to 320-fold, which is markedly superior to the sensitivity of the RPR method. On the other hand, it did not react with the negative sample with any dilution fold.

Example 2

Determination of rheumatoid factor

A rheumatoid factor is an anti-human IgG autoantibody found in a serum of a patient suffering from rheumatoid arthritis and is often cross-reacted with the other animal IgG, particularly, rabbit IgG. The immunogloblin class of the rheumatoid factor is usually IgM, but can be IgG and IgA. The relationship between the immunoglobulin class and cause of the disease is attracted to attention.

Preparation of reagents:

1) Preparation of a latex reagent carrying rabbit IgG thereon;

In 10 ml of tris buffer solution was dissolved 4 mg of rabbit γ-globulin (Fr II, containing 70 to 90% of IgG), and the solution was mixed under stirring for 30 minutes with a suspension of polyvinyltoluene latex (produced by Ceragen Co., particle size: 2.02 μm in diameter) in the tris buffer solution to carry the rabbit γ-globulin on the surfaces of the latex particles. After centrifugation (10000 rpm, 10 minutes), the supernatant was removed and 20 ml of tris buffer solution containing 0.3% bovine serum albumin was added thereto followed by stirrying for 30 minutes to re-disperse it. Further the dispersion was subjected to an ultrasonic wave treatment to highly disperse and stabilize the latex. Subsequently, after centrifugation, it was dispersed in 20 ml of tris buffer solution containing 0.05% of sodium azide and preserved at 4° to 10° C.

2) Preparation of a magnetic material-containing latex reagent carrying anti-IgG, IgA or IgM antibody F (ab')$_2$ thereon;

An antiserum obtained by immunizing rabbit against human IgG, human IgA or human IgM was adsorbed onto Bence Jones protein (χ and λ) to separete a specific antiserum to H-chain of IgG, IgA and IgM. Each of anti-IgG, IgA and Ig M fractions was collected from the resultant antiserum by a conventional method, and then digested with pepsin and subjected to a molecular sieve column chromatography to obtain F (ab')$_2$.

On the other hand, 1 ml of a magnetic material-containing latex (Estapor SML266, particle size: 0.7 μm in diameter, 10%) produced by Rhone poulenc chimie was sufficiently mixed with 19 ml of distilled water followed by centrifugation (10000 rpm, 10 minutes), and then the supernatant was removed to obtain a washed latex pellet. To the pellet was added and dispersed an antibody solution dissolved 4 mg of anti-IgG or anti-IgM antibody F (ab')$_2$ previously prepared in 10 ml of tris buffer. The dispersion was further stirred for one hour to carry F (ab')$_2$ on the surface of the magnetic material-containing latex. The dispersion was centrifuged again to remove the supernatant followed by re-dispersing, suspending and stabilizing with 10 ml of the tris buffer containing 0.3% of bovine serum albumin. The resultant latex was further centrifuged and suspended in 10 ml of tris buffer containing 0.05% of sodium azide, and preserved at 4° to 10° C.

Procedure of the determination:

1) Comparison with RAHA method;

Serum samples of twenty rheumatoid patients, which of titers of which were preliminary estimated by the RAHA method (a method of detecting rheumatoid factor by inspecting the occurance of agglutination of sheep erythrocytes sensitized with rabbit IgG), was diluted to 100-fold by using 0.1% bovine serum albumin and TBS buffer solution. Each of them was apportioned to 3 wells in a microplate with an amount of 100 μl for detecting each class of IgG, IgA and IgM. Thereafter, 50 μl of the rabbit γ-globulin-carrying latex suspension diluted to 8-fold with the tris buffer solution was apportioned to each well, and immediately a side of the microplate was tapped for 10 seconds to mix the contents. It was allowed to stand at a room temperature for 10 minutes to complete the reaction. On the other hand, each of the anti-IgG, anti-IgA and anti-IgM-carrying latex reagents was diluted to 8-fold with the tris buffer solution. They were apportioned with an amount of 50 μl to one of the three wells, respectively. Thereafter, the microplate was tapped as in the above to mix the contents and allowed to stand at a room temperature for 10 minutes to complete the reaction. Then, by means of small sized rod magnets of 3 mm φ a magnetic field was applied to four side walls of the each well of the microplate for 10 minutes to gather the magnetic material-containing latex to side walls. Turbidity of the rabbit γ-globulin-carrying latex suspension which remained in each of the wells without reacting with the magnetic material-containing latex was determined with Microplate Reader (produced by Nippon Intermed Co., NJ-2000) using a light of a wavelength of 620 nm. The experimental results of this example were compared with the titers detected by the RAHA method. The results are shown in Table 2.

TABLE 2

| Sample No. | Title by PAHA method | Data obtained by the present method | | |
|---|---|---|---|---|
| | | IgG | IgA | IgM |
| Control | | 0.490 | 0.502 | 0.526 |
| 3 | <20 | 0.525 | 0.518 | 0.432 |
| 8 | <20 | 0.529 | 0.513 | 0.336 |
| 10 | <20 | 0.526 | 0.525 | 0.514 |
| 12 | 20 | 0.539 | 0.540 | 0.542 |
| 20 | 20 | 0.568 | 0.529 | 0.518 |
| 25 | 40 | 0.538 | 0.477 | 0.497 |

TABLE 2-continued

| Sample No. | Title by PAHA method | Data obtained by the present method | | |
|---|---|---|---|---|
| | | IgG | IgA | IgM |
| 26 | 640< | 0.369 | 0.479 | 0.182 |
| 30 | 40 | 0.535 | 0.561 | 0.420 |
| 31 | 20 | 0.533 | 0.614 | 0.373 |
| 41 | 640< | 0.232 | 0.492 | 0.152 |
| 48 | 320 | 0.342 | 0.157 | 0.311 |
| 52 | 320 | 0.561 | 0.539 | 0.300 |
| 55 | 640< | 0.286 | 0.263 | 0.112 |
| 56 | 640< | 0.472 | 0.576 | 0.186 |
| 89 | 640< | 0.431 | 0.443 | 0.163 |
| 90 | 640< | 0.393 | 0.237 | 0.134 |
| 173 | 640< | 0.225 | 0.175 | 0.127 |
| 400 | 640< | 0.214 | 0.108 | 0.128 |
| 459 | 640< | 0.218 | 0.132 | 0.142 |
| 535 | 640< | 0.515 | 0.406 | 0.159 |

There is a tendency that the specimens of a higher titer is the RAHA method almost show relatively high reactivity, and the relationship of the rheumatoid factor with the IgM class is particularly high.

2) Comparison with EIA method

One sample which had been proved, according to the results of the foregoing determination (1), to contain every class of rheumatoid factors of IgG, IgA and IgM, was selected and diluted with the TBS buffer from 60-fold to 131220-fold stepwisely by 3-fold. A series of these dilutions were in the same manner as in the foregoing procedure (1). The results were compared to those of the EIA method.

The EIA method was conducted as follows: Anti-human IgG, IgA and IgM F(ab')$_2$ which are the same those as carried on the magnetic material-containing latex reagent were labelled with peroxidase according to the method of Mukoujima, "Japan Clinics", Vol 37 Summer season special issue, p. 112 (1979)). A solution 100 μg/ml of rabbit γ-globulin in PBS buffer was adsorbed to a microplate followed by undergoing a treatment with bovine serum albumin-PBS buffer solution to prepare a solid phase. The same sample as the above were diluted from 20-fold to 43740-fold stepwisely by 3-fold. Each of these diluted samples was apportioned to 50 μl well and reacted at 37° C. for 2 hours. Subsequently, after the plate was washed five times with the PBS buffer solution, each 50 μl of the above labelled antibody diluted from 1000 to 2000-fold was apportioned thereto and reacted at 37° C. for 2 hours. After washing with the PBS buffer solution ten times, the resultant was reacted with 4-aminoantipyrine as a color producing agent, at a room temperature for 30 minutes, and an estimation was carried out with Microplate Reader, using a light of a wavelength of 490 nm.

The results are shown in FIGS. 1, 2 and 3.

In the EIA method, when the reactivity is high, the absorbance increases. This means that the higher the dilution fold of the sample becomes, the more the absorbance decreases. In contrast, according to the present invention, the reactivity can be estimated as a degree of decrease in turbidity. This means that the higher the dilution fold of the sample becomes and the lower the reactivity becomes, the more the turbidity increases.

The maximum absorbance in each of the EIA and the present method is about 0.6. It corresponds to the reactivity of 50%. In the sample of the dilution-fold corresponding to the absorbance of 0.3, the method of the present invention is excellent in detection sensitivity as compared with the EIA, i.e. 5-fold in IgG, 90-fold in IgA and 12-fold in IgM, respectively.

What is claimed is:

1. An immunoturbidimetry method of determining the presence of an antibody in a biological fluid sample, comprising the steps of:
   (a) reacting simultaneously with the sample a first reagent comprising insoluble particles having immobilized on the surface thereof an antigen capable of specifically binding to the antibody and a second reagent comprising insoluble magnetic material-containing particles having immobilized on the surface thereof an antibody or fragment thereof which specifically binds to a specific immunoglobulin class, under conditions to promote agglutination of the first and second reagents with the antibody to form an agglutinate;
   (b) separating locally in a reaction system unreacted second reagent and the agglutinate from unreacted first reagent by applying a magnetic field;
   (c) determining the amount of unreacted first reagent; and
   (d) correlating the amount determined in step (c) with the amount of the antibody present in the sample.

2. A method of claim 1, wherein said insoluble particles of the first reagent are selected from the group consisting of cells, gelatin particles, microcapsules, organic polymers, inorganic fine particles and colloidal particles of a metal or a metal compound.

3. A method of claim 2, wherein said organic polymer is polyvinyltoluene or polystyrene.

4. A method of claim 2, wherein said inorganic fine particle is carbon black.

5. A method of claim 1, wherein the antibody which specifically binds to the specific immunoglobulin class is an antibody capable of specifically binding to IgG, IgA, IgD, IgE or L-chains thereof.

6. A method of claim 1, wherein the magnetic material-containing particles of the second reagent comprise a material selected from the group consisting of polysaccharides, proteins, protein derivatives and synthetic polymers.

7. A method of claim 6, wherein said synthetic polymer is obtained by polymerizing an aromatic vinyl compound and/or a methacrylate derivative.

8. A method of claim 1, wherein the magnetic material-containing particles of the second reagent comprise iron or tri-iron tetroxide.

9. A method of claim 1, wherein the magnetic material of the second reagent comprises particles having an average diameter of 10 to 200 Å.

10. A method of claim 1, wherein the content of magnetic material in the magnetic material-containing particles is at least 5% by weight of the magnetic material-containing particles.

11. A method of claim 10, wherein the content of the magnetic material in the magnetic material-containing particles is about 15 to 65% by weight of the magnetic material-containing particles.

12. A method of claim 1, wherein the average diameter of the particles of the first and second reagents is about 0.1 to 10 μm.

13. A method of claim 12, wherein the average particle diameter is about 0.2 to 3 μm.

14. A method of claim 1, wherein the average diameter of the particles of the first reagent is about 0.5 to 3 μm in diameter and that of the second reagent is about 0.2 to 2 μm.

15. A method of claim 14, wherein the average diameter of the particles of the first reagent is about 1 to 2.5 μm and that of the second reagent is about 0.5 to 1.5 μm.

16. A method of claim 1, wherein the ratio of the first reagent to the second reagent is about from 1:20 to 20:1.

17. A method of claim 16, wherein the ratio of the first reagent to the second reagent is from about 1:4 to 4:1.

18. A method of claim 1, wherein the average particle size of the first reagent is about 1 to 2.5 μm in diameter and that of the second reagent is about 0.5 to 1.5 μm in diameter, and the ratio of the first reagent to the second reagent is from 1:0.8 to 1:2.

19. A method of claim 1, wherein the presence of a specific class or subclass of the antibody is detected depending on the occurrence or non-occurrence of the formation of an agglutinate.

* * * * *